United States Defensive Publication [19] (H) [11] T970,005

Palmer et al. [43] May 2, 1978

[54] STABILIZATION OF WET P-BENZOQUINONE WITH METAL CHELATING AGENTS

[76] Inventors: Michael Palmer, 2545 Essex Dr., Kingsport, Tenn. 37660; Ted L. Douglas, Rte. 10, Blakely Dr., Kingsport, Tenn. 37664

[21] Appl. No.: 802,092

[22] Filed: May 31, 1977

[51] Int. Cl.[2] ..... C07C 45/24; C07C 49/64

[52] U.S. Cl. ..... 260/396 R

[57] ABSTRACT

Metal chelating agents such as citric acid can be used to reduce color formation and decomposition of p-benzoquinone containing from 0.1% to 18% moisture level.

1 Claim, No Sheets Drawing,

4 Pages Specification

The file of this unexamined application may be inspected and copies thereof may be purchased (849 O.G. 1221, Apr. 9, 1968).